(12) United States Patent
Siren

(10) Patent No.: US 6,949,517 B1
(45) Date of Patent: Sep. 27, 2005

(54) METHOD OF TREATING INFLAMMATORY, TISSUE REPAIR AND INFECTIOUS CONDITIONS

(76) Inventor: Matti Siren, Snellmansgatan 15 A4, FIN-Helsingfors 17 (FI)

( * ) Notice: Subject to any disclaimer, the term of this patent is extended or adjusted under 35 U.S.C. 154(b) by 0 days.

(21) Appl. No.: 10/635,951

(22) Filed: Aug. 7, 2003

Related U.S. Application Data

(62) Division of application No. 09/876,637, filed on Jun. 7, 2001, now Pat. No. 6,632,797, which is a continuation of application No. 09/202,908, filed as application No. PCT/SE97/01115 on Jun. 23, 1997, now abandoned.

(30) Foreign Application Priority Data

Jun. 24, 1996 (SE) .............................................. 9602463

(51) Int. Cl.$^7$ .............................................. A61K 31/70
(52) U.S. Cl. ............................ 514/23; 514/25; 514/75; 536/1.11
(58) Field of Search ............................ 514/23, 25, 75; 536/1.11

(56) References Cited

U.S. PATENT DOCUMENTS 5,019,566 A * 5/1991 Siren .......................... 514/103

* cited by examiner

Primary Examiner—Elvis O. Price
Assistant Examiner—Michael C. Henry
(74) Attorney, Agent, or Firm—Scully, Scott, Murphy & Presser

(57) ABSTRACT

The present invention relates to a method of treating inflammatory, tissue repair and infectious conditions in a mammal suffering therefrom which comprises administering to a mammal in need thereof an effective amount of a cyclic compound selected from the group consisting of cyclopentane, cyclohexane, cycloheptane, monosaccharide, disaccharide, triaccharide, tetrasaccharide, piperidine, tetrahydrothiopyrian, 5-oxotetrahydrothiopyran, 5,5-dioxotetrahydrothiopyran, tetrahydroselenopyran, tetrahydrofuran, pyrrolidine, tetrahydrothiophene, 5-oxotetrahydrothiophere, 5,5-dioxotetrahydrothiophene, tetrahydroselenophene, benzene, cumene, mesitylene, naphthalene and phenanthrene, in which said cyclic compound is substituted by at least three vicinal phosphorus containing radicals of the formula:

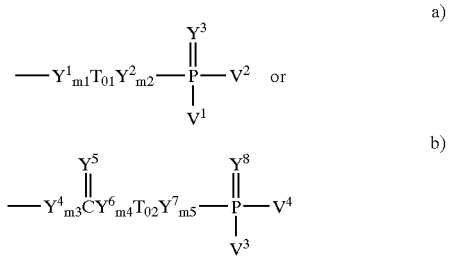

11 Claims, No Drawings

METHOD OF TREATING INFLAMMATORY, TISSUE REPAIR AND INFECTIOUS CONDITIONS

This is a division of U.S. patent application Ser. No. 09/876,637, filed Jun. 7, 2001, now U.S. Pat. No. 6,632,797 which is a continuation of U.S. patent application Ser. No. 09/202,908, filed Oct. 12, 1999, now abandoned, which is a 371 of PCT/SE97/01115 Jun. 23, 1997.

Growth factors comprise a family of polypeptides with a manyfold of properties regulating for example cell proliferation and cell metabolism. As being multi-functional molecules, they may stimulate or inhibit cell proliferation as well as affect cell function depending on the type of the target cells and the presence of other signal peptides. The family of polypeptides include for example platelet derived growth factor (PDGF), epidermal growth factor (EGF), transforming growth factors (TGF-, TGF-β), insulin like growth factors (IGF-1, IGF-2), fibroblast growth factors (a FGF, b FGF), vascular endothelial growth factor (VEGF), nerve growth factor (NGF) and bone morphogenetic proteins (BMP)

The activities of these growth factors are considered to be casual components of several conditions such as cardiovascular conditions, for example diabetes, inflammatory conditions for example rheumatoid arthritis, analgetic conditions, viral conditions carcinogenic conditions, several eye diseases and would healing.

Angiogenesis is under normal conditions under stringent control but in many pathological conditions e.g. solid tumours, rheumatoid arthritis, diabetic retinopathy and artherosclerosis unregulated vessel proliferation occurs. The angiogenetic process is controlled by a balance between many positive and negative regulating signals where growth factors such as TGF, FGF and VEGF play a dominant role.

Under normal conditions in the body growth factor activity is to a large extent regulated by the interactions with heparin and heparan sulfate. The interaction between these polyanionic glycosaminoglycans and growth factors is through to be of functional significance serving as storage depots for growth factors and protecting them from various degradative processes (Vlodavsky, I., Fuks, Z., Ishai-Michaeli, R., Bashkin, P., Levi, E., Korner, G., Bar-Shavit, R., and Klagsbrun, M. (1991) *J. Cell Biochem.* 45, 167–176)

Under some circumstances the administration of growth factors as therapeutic agents has been utilized. However the limited stability of this type of molecules reduces their activity before reaching the target in the body.

Under abnormal conditions when growth factor regulation is required to a larger extent than in the normal situation, the administration of heparin and derivatives of heparin has been considered. However the administration of these type of compounds renders side-effects like antiocoagulant activity which limits their possible usage.

Other sulphonated compounds like suramin, a polysulphonated napthylurea, has been shown to have activity in the treatment of adrenocortical carbinoma but the limitation also for this type of compounds is the narrow margin between the dose required to achieve anti-tumor activity and the dose leading to the onset of toxic side effects.

According to the present invention the use of a compound containing a high density, negatively charged domain of vicinally oriented radicals for the preparing of a medicament providing a growth factor modulating activity in mammals including man is described.

In preferred embodiments of the invention the negatively charged domain comprises, at least three vicinal phosphorus-containing radicals.

The invention also relates to the use of a compound wherein the phosphorus-containing radicals have the following formula:

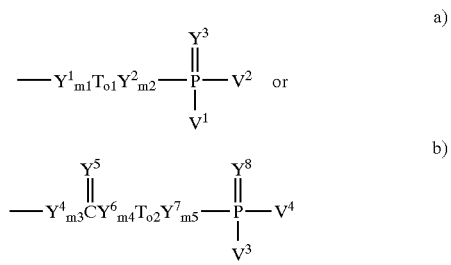

wherein
$V^1$ to $V^4$ are $Y^8_{m6} T_{o3} U$
$T_{o1}$ to $T_{o3}$ are $(CH_2)_n$, CHCH, or $CH_2CHCHCH_2$,
o1 to o3 are 0 or 1,
n is 0 to 4,
U is $R^1Y^9_{m7}$, $CY^{10}Y^{11}R^2$, $SY^{12}Y^{13}Y^{14}R^3$, $PY^{15}Y^{16}Y^{17}R^4R^5$,
$Y^{18}PY^{19}Y^{20}Y^{21}R^6R^7$, $CH_2NO_2$, $NHSO_2R^8$, or $NHCY^{22}Y^{23}R^9$,
m1 to m7 are 0 to 1,
$Y^1$ to $Y^{23}$ are $NR^{10}$, $NOR^{11}$, O, or S,
and where $R^1$ to $R^{11}$ are
i) hydrogen
ii) a straight or branched saturated or unsaturated alkyl residue containing 1–22 carbon atoms
iii) a saturated or unsaturated aromatic or non-aromatic homo- or heterocyclic residue containing 3–22 carbon atoms and 0–5 heteroatoms consisting of nitrogen, oxygen sulfur
iv) a straight or branched saturated or unsaturated alkyl residue containing 1–22 carbon atoms substituted with a saturated or unsaturated aromatic or non-aromatic homo- or heterocyclic containing 3–22 carbon and 0–5 heteroatoms consisting of nitrogen, oxygen or sulfur
v) an aromatic or non-aromatic homo- or heterocyclic residue containing 3–22 carbon and 0–5 heteroatoms consisting of nitrogen, oxygen or sulfur substituted with a straight or branched saturated or unsaturated alkyl residue containing 1–22 carbon atoms in the said groups ii–v the residues and/or the substituents the thereof being substituted with 0–6 of the following groups: hydroxy, alkoxy, aryloxy, acyloxy, carboxy, alkoxycarbonyl, alkoxycarbonyloxy, aryloxycarbonyl, carbamoyl, fluoro, chloro, bromo, azido, cyano, oxo, oxa, amino, imino, alkylamino, arylamino, acylamino, arylazo, nitro, alkylthio or alkylsulfonyl The streight or branched saturated or unsaturated alkyl residue in groups i–v above can be exemplified by methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, doeicosyl, isopropyl, isobutyl, isopentyl, isohexyl, isoheptyl, isooctyl, isononyl, isodecyl, isodoecosyl, 2-butyl, 2-pentyl, 2-hexyl, 2-heptyl, 2-octyl, 2-nonyl, 2-decyl, 2-doeicosyl, 2-methylbutyl, 2-methylpentyl, 2-methylhexyl, 2-methylheptyl, 2-methyloctyl, 2-methylnonyl, 2-methyldecyl, 2-methyleiocosyl, 2-ethylbutyl, 2-ethylpentyl, 2-ethylhexyl, 2-ethylheptyl, 2-ethyloctyl, 2-ethylnonyl, 2-ethyldecyl, 2-ethyleicosyl, tertbutyl, ethenyl, propenyl, butenyl, pentenyl, hexenyl, heptenyl, octenyl, nonenyl, decenyl undecenyl, dodecenyl, tridecenyl, tetradecenyl, pentadecenyl, hexadecenyl, heptadecenyl, octadecenyl, nonadecenyl, eicosenyl, heneicosenyl, doeicosenyl, butadienyl, pentadienyl, hexadienyl, heptadienyl, octadienyl, nonadienyl, decadienyl, doeicodienyl, ethynyl, propynyl, doeicosynyl.

The saturated or unsaturated aromatic or non-aromatic homo- or heterocyclic residue in groups i–v above can be exemplified by cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, cyclohexadecyl, cycloheptadecyl, cyclooctadecyl, cyclononadecyl, cycloeicosyl, cycloheneicosyl, cyclodoeicosyl, adamantyl, cyclopropenyl, cyclobutenyl, cyclopentenyl, cyclohexenyl, cycloheptenyl, cyclooctenyl, cyclononenyl, cyclodecenyl, phenyl, biphenyl, napthyl, hydroxyphenyl, aminophenyl, mercaptophenyl, fluorophenyl, chlorophenyl, azidophenyl, cyanophenyl, carboxyphenyl, alkoxyphenyl, acyloxyphenyl, acylphenyl, oxiranyl, thiiranyl, aziridinyl, oxetanyl, thietanyl, azetidinyl, tetrahydrofuranyl, tetrahydrothiophenyl, pyrrolidinyl, tetrahydropyranyl, tetrahydrothiopyranyl, piperidinyl, quinuclidinyl, dioxanyl, dithianyl, trioxanyl, furyl, pyrrolyl, thienyl, pyridyl, quinolyl, benzofuryl, indolyl, benzothienyl, oxazolyl, imidazolyl, thiazolyl, pyridazinyl, pyrimidyl, pyrazinyl, purinyl, or a carbohydrate.

Substituents may be selected from the group of: hydroxy, alkoxy, aryloxy, acyloxy, carboxy, alkoxycarbonyl, alkoxycarbonyloxy, aryloxycarbonyl, aryloxycarbonyloxy, carbamoyl, fluoro, chloro, bromo, azido, cyano, oxo, oxa, amino, imino, alkylamino, arylamino, acylamino, nitro, alkylthio, alkylsulfonyl.

Furthermore the invention relates to the use of a compound wherein the phosphorus-containing radicals have the following formula:

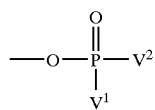

wherein $V^1$ and $V^2$ are the same of different and are OH, $(CH_2)_pOH$, COOH, $CONH_2$, CONOH,
$(CH_2)_pCOOH$, $(CH_2)_pCONH_2$, $(CH_2)_pCONOH$, $(CH_2)_pSO_3H$,
$(CH_2)_pSO_3NH_2$, $(CH_2)_pNO_2$, $(CH_2)_pPO_3H_2$, $O(CH_2)_pOH$,
$O(CH_2)_pCOOH$, $O(CH_2)_pCONH_2$, $O(CH_2)_pCONOH$, $O(CH_2)_pSO_3H$,
$O(CH_2)_pSO_3NH_2$, $O(CH_2)_pPO_3H_2$ or $CF_2COOH$
p is 1 to 4

In this embodiment of the invention the phosphorus-containing radicals are phosphonates or phospates or derivatives thereof.

In one embodiment of the invention the backbone to the high density negatively charged region of vicinally oriented radicals is a cyclic moiety.

The cyclic moiety comprises a saturated or unsaturated aromatic or non-aromatic homo- or heterocyclic moiety. When the moiety is heterocyclic the heteroatoms are selected from the group of oxygen, nitrogen, sulfur or selenium.

Preferably the cyclic moiety comprises 4 to 24 atoms, most preferably 5 to 18 atoms. The cyclic moiety is for example selected from the group of cyclopentane, cyclohexane, cycloheptane, cyclooctane, inositol, monosacharide, disacharide, trisacharide, tetrasacharide, piperidin, tetrahydrothiopyran, 5-oxotetrahydrothiopyran, 5,5-dioxotetrahydrothiopyran, tetrahydroselenopyran, tetrahydrofuran, pyrrolidine, tetrahydrothiophene, 5-oxotetrahydrothiophene, 5,5-dioxotetrahydrothiophene, tetrahydroselenophene, benzene, cumene, meirtylene, naphtalene and phenantrene. When the cyclic moiety is an inositol it could be selected from the group of alloinositol, cisinositol, epiinositol, D/L-chiroinositol, scylloinositol, myoinositol, mucoinositol and neoinositol.

In one preferred embodiment of the invention the compounds are phosphates, phosphonates or phosphinates of cyclohexane such as 1, 2, 3β-cyclohexane-1,2,3-trioltrisphosphate.

In other preferred embodiments of this type of the invention the compounds are phosphates, phosphonates or phosphinates of inositol. Preferably the number of phosphate-, phosphonate- or phosphinate radicals per inositol moiety is at least three. The remaining hydroxyl groups on the inositol moiety may be derivatized in the form of ethers or esters.

In one preferred embodiment the compound is myo-inositol-1,2,6-trisphosphate or myo-inositol-1,2,3-trisphosphate In one most preferred embodiment the compounds are selected from the group of D-myo-inositol-1,2,6-trisphosphate, D-myo-inositol-1,2,6-tris (carboxymethylphosphate), D-myo-inositol-1,2,6-tris (carboxymethylphosphonate), D-myo-inositol-1,2,6-tris (hydroxymethylphosphonate), D-3,4,5-tri-O-methyl-myo-inositol-1,2,6-trisphosphate, D-3,4,5-tri-O-hexanoyl-myo-inositol-1,2,6-trisphosphate, D-3,4,5-tri-O-butanoyl-myo-inositol-1,2,6-trisphosphate, D-3,4,5-tri-O-pentanoyl-myo-inositol-1,2,6-trisphosphate, D-3,4,5-tri-O-isobutanoyl-myo-inositol,1,2,6-tris-phosphate, D-3,4,5-tri-O-propanoyl-myo-inositol-1,2,6-trisphosphate, D-3,4,5-tri- O-(6-hydroxy-4-oxa)hexanoyl-myo-inositol-1,2,6trisphosphate, D-3,4,5-tri-O3- (ethylsulphonyl)propanoyl-myo-inositol-1,2,6-trisphosphate, D-3,4,5-tri-O-3- hydroxypropanoyl-myo-inositol-1,2,6-trisphosphate, D-3,4,5-tri-O-(6-hydroxy)-hexanoyl-myo-inositol-1,2,6-trisphosphate, D-5-O-hexanoyl-myo-inositol-1,2,6- trisphosphate, D-3,4,5-tri-O-phenylcarbamoyl-myo-inositol-1,2,6-trisphosphate, D-3,4,5-tri-O-propanoyl-myo-inositol-1,2,6-tris (carboxymethylphosphate), D-3,4,5-tri-O-butanoyl-myo-inositol-1,2,6-tris(carboxymethylphosphate), D-3,4,5- tri-O-isobutanoyl-myo-inositol-1,2,6-tris(carboxymethyl-phosphate), D3,4,5-tri-O- pentanoyl-myo-inositol-1,2,6-tris (carboxymethylphosphate), D-3,4,5-tri-O- hexanoyl-myo-inositol-1,2,6-tri(carboxymethylphosphate), D-3,4,5-tri-O-pro- panoyl-myo-inositol-1,2,6-tris (carboxymethylphosphonate), D-3,4,5-tri-O- butanoyl-myo-inositol-1,2,6-tris(carboxymethylphosphonate), D-3,4,5-tri-O-iso- butanoyl-myo-inositol-1,2,6-tris (carboxymethylphosphonate), D-3,4,5-tri-O- pentanoyl-myo-inositol-1,2,6-tris(carboxymethylphosphonate), D-3,4,5-tri-O- hexanoyl-myo-inositol-1,2,6-tris (carboxymethylphosphonate), D-3,4,5-tri-O- propanoyl-myo-inositol-1,2,6-tris(hydroxymethylphosphonate), D-3,4,5-tri-O- butanoyl-myo-inositol-1,2,6-tris (hydroxymethylphosphonate), D-3,4,5-tri-O- isobutanoyl-myo-inositol-1,2,6-tris(hydroxymethylphosphonate), D-3,4,5-tri-O- pentanoyl-myo-inositol-1,2,6tris (hydroxymethylphosphonate), D-3,4,5-tri-O- hexanoyl-myo-inositol-1,2,6-tris(hydroxymethylphosphonate).

When the cyclic moiety is a sacharide it could be selected from the group of D/L- ribose, D/L-arabinose, D/L-xylose, D/L-lyxose, D/L-allose, D/L-altrose, D/L- glucose, D/L-mannose, D/L-gulose, D/L-idose, D/L-galactose, D/L-talose, D/L- ribulose, D/L-xylulose, D/L-psicose, D/L- sorbose, D/L-tagatose and D/L-fructose or derivatives thereof. In preferred embodiments of this type of the invention the compounds are phosphates, phosphonates, or phosphinates of sacharides. Preferably the number of phosphate-, phosphonate- or phosphinate radicals per sacharide units is at least three. The remaining hydroxyl groups on the sacharide moiety may be derivatized in the form of ethers or esters. In many instances the ether form is desired as this type of radical propongs the stability and half-life in vivo as the susceptibility to enzymatic degradation is reduced. In one preferred embodiment of this type of the invention the compound is selected from the group of mannose-2,3,4-trisphosphate, galactose-2,3,4-trisphosphate, fructose-2,3,4--trisphosphate, altrose-2,3,4-trisphosphate and rhamnose-2,3,4-trisphosphate. In one most preferred embodiment the compound is selected from the group of $R_1$-6-O-$R_2$-α-D-mannopyranoside-2,3,4-trisphosphate, $R_1$-6-O-$R_2$-α-D-galacto- pyranoside-2,3,4-trisphosphate, $R_1$-6-O-$R_2$-α-altropyranoside-2,3,4-trisphosphate and $R_1$-6-O-$R_2$-β-D-fructopyranoside-2,3,4-trisphosphate where $R_1$ and $R_2$ independently are as defined above and preferably are methyl, ethyl, propyl, butyl, pentyl or hexyl. Most preferred compounds in this type of the invention are methyl-6-O-butyl-α-D-mannopyranoside-2,3,4-trisphosphate, methyl-6-O-butyl-α- -D-galactopyranoside-2,3,4-trisphosphate, methyl-6-O-butyl-α-D-glycopyranoside- -2,3,4-trisphosphate, methyl-6-O-butyl-α-D-altropyranoside-2,3,4-trisphosphate, methyl-6-O-butyl-β-D-fructopyranoside-2,3,4-trisphosphate, 1,5-anhydro-D-arabinitol -2,3,4-trisphosphate, 1,5-anhydroxylitol-2,3,4-trisphosphate, 1,2-O-ethylene- -β-D-fructopyranoside-2,3,4-trisphosphate, methyl-α-D-rhamnopyranoside-2,3,4- -trisphosphate, methyl-α-D-mannopyranoside-2,3,4-triphosphate, methyl-6-O-butyl-α-D-mannopyranoside-2,3,4-tris-(carboxymethylphosphate), methyl-6-O-butyl-α-D-mannopyranoside-2,3,4-tris-(carboxymethylphosphonate), methyl-6-O-butyl-α-D-mannopyranoside-2,3,4-tris(hydroxymethylphosphonate), methyl-6-O-butyl-α-D-galactopyranoside-2,3,4-tris(carboxymethylphosphate), methyl-6-O-butyl-α-D-galactopyranoside-2,3,4-tris(carboxymethylphosphonate), methyl-6-O-butyl-α-D-galactopyranoside-2,3,4-tris(hydroxymethylphosphonate), methyl-6-O-butyl-α-D-glucopyranoside-2,3,4-tris(carboxymethylphosphate), methyl-6-O-butyl-α-D-glucopyranoside-2,3,4-tris(carboxymethylphosphonate), methyl-6-O-butyl-α-D-glucopyranoside-2,3,4-tris(hydroxymethylphosphonate), methyl-6-O-butyl-α-D-altropyranoside-2,3,4-tris-(carboxymethylphosphate), methyl-6-O-butyl-α-D-altropyranoside-2,3,4-tris-(carboxymethylphosphonate), methyl-6-O-butyl-α-D-altropyranoside-2,3,4-tris-(hydroxymethylphosphonate), methyl-6-O-butyl-β-D-fructopyranoside-2,3,4-tris-(carboxymethylphosphate), methyl-6-O-butyl-β-fructopyranoside-2,3,4-tris-(carboxymethylphosphonate), methyl-6-O-butyl-β-fructopyranoside-2,3,4-tris-(hydroxymethylphosphonate).

In other preferred embodiments of the invention the compounds are phosphates, phosphonates or phosphinates of heterocyclic moieties such as 1,5-dideoxy-1,5-iminoarabinitol-2,3,4-trisphosphate, 1,5-dideoxy-1,5-iminoarabinitol-2,3,4-tris- (carboxymethylphosphate), 1,5-dideoxy-1,5,-iminoarabinitol-2,3,4-tris(carboxymethylphosphonate), 1,5-dideoxy-1,5-iminoarabinitol-2,3,4-tris(hydroxymethyl- phosphonate), 1,5-dideoxy-1,5-imino-N-(2-phenylethyl)arabinitol-2,3,4-trisphosphate, 1,5,--dideoxy-1,5,-imino-N-(2-phenylethyl)arabinitol-2,3,4-tris(carboxy- methylphosphate), 1,5-dideoxy-1,5-imino-N-(2-phenylethyl)arabinitol-2,3,4-tris- (carboxymethylphosphonate), 1,5-dideoxy-1,5-imino-N-(2-phenylethyl) arabinitol- 2,3,4-tris(hydroxymethylphosphonate).

The growth factor modulating activity of the described compounds are expressed on at least four levels. One level is a type of interaction with growth factors such as heparin-binding growth factors and/or the specific receptors of these growth factors. The compounds according to the invention interact with domains comprising high basicity on the growth factors. This type of interaction is considered to be an important factor in connection with growth factors such as basic fibroblast growth factor, acidic fibroblast growth factor, platelet-derived growth factor, vascular endothelial growth factor and hepatocyte growth factor.

The interactions are considered to be especially important in connection with growth factors from the fibroblast growth family such as different types of acidic and basic fibroblast growth factors. Processes which are regulated by the interaction are e.g. dimerization and interactions with receptors and ligands.

Another level of interaction is a more specific interaction with the internalisation process of a group of growth factors. Many growth factors are exerting their effect after internalisation to the intracellular domain. The pathway includes an interaction/binding of the growth factor to the external part of a transmembrane receptor. Binding is followed by endocytosis i.e. the formation of a vesicle which is transferred over the plasma membrane and released into the internal part of the cell. This process of internalisation is controlled by specific assembly proteins. One specific assembly protein, AP-2 is considered to be important in the internalisation process of this group of growth factors. Within the scope of the invention it is considered that the described compounds interact with the external receptor and an ion-channel connected to AP-2. the binding of this group of growth factors to their receptor is effected by interaction with receptor bound small monophosphorylated sugars such as mannose-phosphate. When the binding to the monophosphorylated sugar is reversed by the existence of compounds according to the invention, the binding of the growth factor is retarded or does not happen at all.

The other interaction on this level is the binding of the compounds according to the invention to an ion-channel, most often a potassium-channel belonging to AP-2. Such a binding retards or in some case inhibit the internalisation process and thus retards or inhibits the consequences of growth factors entering the internal part of the cell and the subsequent metabolic events. To the group of growth factors functioning according to the described pathway belong for example epidermal growth factor, transforming growth factor, insulin growth factor and nerve growth factor.

A third level of interaction includes a very specific interaction between the compounds according to the invention and a specific group of growth factors. The negatively charged domain of the compounds according to the invention interacts with domains in the growth factor, characterized by the existence of basic amino acids such as arginine, lysine and histidine structurally arranged in a way that renders condensed binding sites on a small area. The binding area is typically not exceeding 500 square Angstrom and requires a specific sterochemistry of the binding compound. Accordingly, the preferred compounds have two equatorial and one axial equatorial negatively charged groups attached to a cyclic moiety. Within this group of growth factors transforming growth factor β is mentioned as one example. The interaction is for example expressed by three lysine moieties, lysine 25, lysine 31 and lysine 37 and three phosphate radicals in a way that the distance between the radicals is less than 10 Angstrom.

The interaction between the growth factors and compounds according to the invention is characterized by a binding constant, $K_D$. Typically, the $K_D$ value is less than 100 $\mu$M. Preferably the binding constant is less than 60 $\mu$M and most preferably less than 30 $\mu$M.

The interaction is also described as a consequence of the acid constants, $pK_{A1}$ of the compounds according to the invention. Typically $pK_{A1}$ is in the range of 7 to 9 and for some compounds in the range of 7 to 12.

A fourth level of interaction is expressed by a receptor interaction on the cell surface which transfer the signal from for example a specific growth factor via a signalling cascade to the internal compartments of the cell. The compounds bind to the receptor on the cell surface characterized by a $IC_{50}$-value less than 50 $\mu$M and preferably less than 5 $\mu$M. The binding is depending on the concentration, either allosteric or hyperbolic.

The effects described renders the growth factor modulating activity which is characteristic to the use of the compounds according to the invention.

According to the invention the compounds are most often present in a salt form or in a form where only a few of the negative charges are protonated. The salt can contain one or more cations in different combinations. Examples of cations are sodium and potassium ions.

The pharmaceutical composition according to the invention may be administered orally, topically, parentally, rectally or by inhalation spray in dosage forms or formulations comprising conventional, non-toxic pharmaceutically acceptable carriers, adjuvants and vehicles.

The pharmaceutical composition for oral use can be present in different forms such as capsules, granules, tablets, troches, lozenges, aqueous suspensions, dispensible powders, emulsions, syrups or elixirs. When the composition is present in liquid form capsules are preferably utilized. At the use of granules, there preferably have a size of 0.15–2 mm. Either the granules can consist of the pharmaceutical composition per se or of the composition and suitable fillers. When the pharamceutical composition is used in a tablet form, the tablets can have a weight of 50–1500 mg, preferably 50–800 mg and most preferably 100–500 mg.

Formulations for oral use include tablets which contain the active ingredient in a mixture with non-toxic pharmaceutically acceptable excipients. These excipients may be, for example, inert diluents, such as calcium carbonate, sodium chloride, lactose, calcium phosphate or sodium phosphate, granulating and disintegrating agents, for example, potato starch, or alginic acid, binding agents, for example, starch, gelatin or acacia, and lubricating agents, for example, magnesium stearate, stearic acid or talc. The tablets may be uncoated or they may be coated by known techniques to delay disintegration and absorption in the gastrointesinal tract and thereby provide a sustained action over a longer period. For example, a time delay material such as glyceryl monostearate or glyceryl distearate may be employed.

Formulations for oral use may also be presented as hard gelatin capsules wherein the activ ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

For the parentaral application of the composition of this invention, typical dosage forms include intravenous, intramuscular, intraperitoneal formulations.

For the rectal application of the composition of this invention, typical dosage forms include suppositories, rectal gelatin capsules (solutions and suspensions), and enemas or micro-enemas (solutions and suspensions). Thus, in a typical suppository formulation, any one of the compounds of this invention is combined with any pharmaceutically acceptable suppository base such as cocoa butter, esterified fatty acids, glycerinated gelatin, and various water-soluble or dispersible bases like polyethylene glycols and polyoxyethylene sorbitan fatty acid ester. Various additives like salicylates or surfactant materials may be incorporated.

For topical use, creams, ointments, gels, solutions or the like containing the compositions are employed according to methods recognized in the art.

Naturally, the therapeutic dosage range for the compounds of the present invention will vary with the size and needs of the patient and the particular condition or disease symptom being treated.

The administration of the pharmaceutical composition according to the invention can be in a combined dosage form or in separate dosage forms.

For administration to human patients appropriate dosages can routinely be determined by those skilled in this art by extension of the results obtained in animals at various dosages. The preferred dosage for humans falls within the range of 0.1 to 100 mg compound per day and kg bodyweight, especially 0.1 to 50 mg/day/kg bodyweight.

The administration of the compounds according to the invention to mammals are considered to be beneficial within the following conditions:

Bond disorders such as heterotopic ossification, osteoporosis, osteoarthritis, osteomalacia, Paget's disease.

Inflammatory conditions such as rheumatoid arthritis

Analgesic conditions such as hyperalgesia

Tumour conditions such as glioma, prostate cancer and other conditions where inhibition of angiogenesis is crucial Wound healing or tissue repair such as matrix formation, collagen synthesis and scarr formulation Viral conditions such as HIV Cardiovascular conditions such as atherosclerosis Eye diseases Infectious conditions such as trypanosomiasis According to the present invention a process of modulating growth factor activity by using a compound containing a high density, negatively charged domain of vicinally oriented radicals is described.

In preferred embodiments of the invention the negatively charged domain comprises at least three vicinal phosphorus-containing radicals.

The invention also relates to the use of a compound wherein the phosphorus-containing radicals have the following formula:

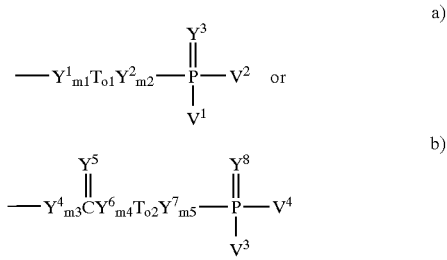

as described above.

The invention will be further explained with the following embodiment examples however without limiting it thereto.

Example 1 and 2 describe the interaction between growth factors and D-myo- inositol-1,2,6-trisphosphate (IP$_3$). In example 3 and 4 the growth factor modulating effect of IP$_3$ in tumor models are illustrated while example 5 describes the counteraction of heterotopic bone formation by IP$_3$.

Example 6 shows the inhibitory effect of D-3,4,5-tri-O-hexanoyl-myo-inositol- 1,2,6-trisphosphate (PP10-202) on HIV-infection.

Example 7 describes a growth factor modulating effect of IP$_3$ in oedema conditions while example 8, 9 and 10 illustrate the growth factor modulating effect of 1,2O-ethylene-β-D-fructopyranoside 2,3,4-trisphosphate (PP 35-405), 1,5-dideoxy- 1,5-imino-N-(2(phenylethyl) arabinitol-2,3,4-trisphosphate (PP 35-508) and myo-inositol-1,2,6-tris(carboxymethylphosphonate) (PP 40-402), respectively in inflammatory conditions.

In example 11 the growth factor modulating effect of IP$_3$ in eye opening of mice is examined.

The effect of the application of IP$_3$ on scarring is shown in example 12. Example 13 describes the interaction between assembly protein-2 (AP-2) and IP$_3$. Example 14 illustrates the binding of compounds accordings to the invention to spermine, while example 15 shows the analgetic effect of methyl-α-D-rhamnopyranoside- 2,3,4-trisphosphate (PP 35-406). Example 16 describes the effect of IP$_3$ on PI 3'- kinase. The effect of IP$_3$ against bone tumours is described in Example 17. Example 18 illustrates the inhibitory effect of IP$_3$ against b FGF-induced damages, while Example 19 describes the interaction between IP$_3$ and different fibroblast growth factors in computer modelling experiments.

EXAMPLE 1

Nerve growth factors (NGFA from Vipera lebetina Venom and NGFB from Mouse Submaxillary glands) 0.31 nmol and 0.08 nmol respectively) were mixed with 2.7 nmol of radioacitve D-myo-inositol-1,2,6-trisphosphate (IP$_3$) (specific activity 17 Ci/mmol) and diluted with a buffer containing 50 mM Hepes and 1 mM EDTA, pH 7 4 to a final volume of 1 ml. The mixture was incubated for 1 hour at 4° C.

The interaction between NGF and IP$_3$ was determined by factioning the incubate on a Sephadex G-25 column (Pharmacia Biotech, Sweden) (volume 9.1 ml, bed height 5 cm). This type of column fractionate substances according to molecular weight. Substances with molecular weight exceeding 1500 will not penetrate the microspheres of the column and will accordingly elute quite soon after being loaded to the column, while smaller molecules will appear later as they partly or totally penetrate the microspheres depending on the molecular weight. Thus a mixture of a polypeptide such as NGF (Mw≧1500) and a substance with Mw 500, such as IP$_3$ will elute in two separated peaks if there is no interaction between the substances.

The incubate was loaded on the column and was eluted with 50 mM Hepes in fractions of 0.4 ml each. Each fraction was determined for radioactivity, indicating the occurrence of IP$_3$ and with UV (280 nm) indicating the occurrence of NGF. Maximum radioactivity and UV absorbance was measured in the same fraction, number 10, indicating that the two components eluted together.

To further determine the interaction, the fractions with radioactivity and UV-absorbance were loaded on a Heparin-Sepharose CL-6B column (Pharmacia Biotech, Sweden) (volume 25 ml, height 20 cm). As heparin is known to strongly interact with growth factors such as NGF this type of column is able to bind NGF while other substances such as IP$_3$ will be eluted. Elution was performed with 50 mM Hepes, pH 7.4 and each fraction of 1 ml was collected for determination of radioactivity and UV absorbance. A peak with radioactivity but without UV absorption was loaded on a similar Sephadex G-25 column as described above and was eluted with the same type of buffer. Maximum radioactivity was obtained in fraction number 13 i.e. in this case the substance with radioactivity was more retained on the column.

The experiment shows that there exists a strong interaction between NGF and IP$_3$. When eluted from a Sephadex G-25 column they elute together, demonstrating the interaction. After binding NGF to a Heparin-Sepharose column, IP$_3$ without NGF elutes at a different place after passage through a Sephadex G-25 column showing that this type of column is capable of differing between the NGF-IP$_3$ complex and pure IP$_3$.

EXAMPLE 2

Fibroblast growth factor (FGF) (0.027 nmol) was mixed with 2.7 nmol of radioactive D-myo-inositol-1,2,6-trisphosphate (IP$_3$) specific activity 17 Ci/mmol) and diluted with a buffer containing 50 mM Hepes and 1 mM EDTA, pH 7.4 to a final volume of 1 ml. The mixture was incubated for 1 hours at 4° C.

The interaction between FGF and IP$_3$ was determined by fractioning the incubate on a Sephadex G-25 column (Pharmacia Biotech, Sweden) (volume 9.1 ml, bed height 5 cm). This type of column fractionate substances according to molecular weight. Substances with molecular weight exceeding 1500 will not penetrate the microspheres of the column and will accordingly elute quite soon after being loaded to the column, while smaller molecules will appear later as they partly or totally penetrate the microspheres depending on the molecular weight. Thus a mixture of a polypeptide such as FGF (Mw≧1500) and a substance with Mw 500, such as IP$_3$ will elute in two separated peaks if there is no interaction between the substances.

The incubate was loaded on the column and was eluted with 50 mM Hepes in fractions of 0.4 ml each. Each fraction was determined for radioactivity, indicating the occurrence of IP$_3$ and with UV (280 nm) indicating the occurrence of FGF. Maximum radioactivity and UV absorbance was measured in the same fraction, number 10, indicating that the two components eluted together.

To further determine the interaction the fractions with radioactivity and UV absorbance were loaded on a Heparin-Sepharose CL-6B column (Pharmacia Biotech Sweden) (volume 25 ml, height 20 cm). As heparin is known to strongly interact with growth factors such as FGF this type of column is able to bind FGF while other substances such as IP$_3$ will be eluted. Elution was performed with 50 mM Hepes, pH 7.4 and each fraction of 1 ml was collected for determination of radioactivity and UV absorbance. A peak with radioactivity but without UV absorption was loaded on a similar Sephadex G-25 column as described above and was eluted with the same type of buffer. Maximum radioactivity was obtained in fraction number 13 i.e. in this case the substance with radioactivity was more retained on the column.

The experiment shows that there exists a strong interaction between FGF and IP$_3$. When eluted from a Sephadex G-25 column they elute together, demonstrating the interaction. After binding FGF to a Heparin-Sepharose column IP$_3$ without FGF elutes at a different place after passage through a Sephadex G-25 column showing that this type of column is capable of differing between the FGF-IP$_3$ complex and pure IP$_3$.

EXAMPLE 3

The aim of this experiment was to investigate the effect of IP$_3$ in a model ressembling a clinical situation in injured tissue where fibroblast growth factors mediate autocrine and paracrine cell growth phases.

Fibroblast growth factor acidic (aFGF) from Sigma (USA), was diluted in a buffer, RPMI-1640 (Life Technologies, UK) 25 μg of aFGF was diluted in 125 μl buffer, and 50 μl was transferred to a small Eppendorf tube. 150 μl of Matrigel® basement membrane matrix from Becton and Dickinson (UK) was added to the tube and the content was thoroughly mixed for 60 minutes. All equipment was sterilized by irradiation or autoclaving (115° C. in 10 minutes) before use and all procedures were performed at 7° C. The mixture was kept in an icebath before the animal experiment.

Ten female, specific pathogen free BALBc nude mice with a weight of 18–22 were maintained in autoclaved type III makrolon cages with filter tops in horizontal air flow cabinets in a barrier unit equipped with HEPA filters. Autoclaved bedding, irradiated feed and sterile filtered water was used. Temperature and humidity was kept constant at 22±2° C, 65±5 RH.

When fibroblast growth factor (FGF) and Matrigel® is mixed and inovulated to nude mice, developments of a swelling process ressembling tumor begin to develop.

A portion of the mixture of Matrigel® and a FGF was inoculated subcutaneously by a 23 G needle in the right flank of the mice. Two days before all mice were surgically prepared with osmotic minipumps (Alzet, model 2002). To five mice, D-myo-inositol-1,2,6-trisphosphate (IP$_3$) was administered (pump volume 226 μl, duration 14 days, concentration 0.4 g/ml).

To another group of five mice saline was administered as a control group.

The volume of the formed matrix was measured during 9 days and the results are shown in the following table.

|     | Treatment | |
| --- | --- | --- |
| Day | IP$_3$ volume (mm$^3$) | Control volume (mm$^3$) |
| 1 | 150 | 150 |
| 4 | 125 | 125 |
| 5 | 90 | 125 |
| 6 | 50 | 130 |
| 7 | 50 | 140 |
| 8 | 70 | 130 |
| 9 | 70 | 120 |

The results show a marked reduction in the aFGF-induced swelling process when the animals were treated with IP$_3$. The administration of IP$_3$ in vivo counteracts produced and released a FGF which indicate clinically favourable effects of the compound as a FGF-induced processes are basic phenomenons in different phases of many diseases.

EXAMPLE 4

In a procedure similar to example 3 fibroblast growth basic (bFGF) was used.

D-myo-inositol-1,2,6-trisphosphate (IP$_3$) was administered to five mice while another group of five mice, recieving saline, were a control group.

The volumes of the formed matrix were measured during 9 days and the results are shown in the following table:

|     | Treatment | |
| --- | --- | --- |
| Day | IP$_3$ volume (mm$^3$) | Control volume (mm$^3$) |
| 1 | 180 | 220 |
| 3 | 120 | 140 |
| 5 | 110 | 150 |
| 7 | 120 | 170 |
| 8 | 110 | 200 |
| 9 | 120 | 200 |

The treatment with IP$_3$ reduces the volume of the tumor compared to control in a marked way demonstrating the down-regulatory effect of IP$_3$ on bFGF-induced injuries. Histological examinations of the animals revealed anti-angiogenic effects in the group where IP$_3$ was administered.

EXAMPLE 5

Using the rabbit heterotopic bone (HB) development model, the aim of this experiment was to investigate the effect of D-myo-inositol-1,2,6-phosphate (IP$_3$) against heterotopic bone formation. Heterotopic bone formation is caused by a local growth and formation of bone. One essential component in this process is the activation of growth factors.

The right hind limb of adult rabbits (weight about 4.0 kg) was immobilized with the knee in extension by means of a plastic splint and an elastic bandage, so that the Vastus intermedius profundus (VIP) muscle was in a shortened position and the hip joint could be moved freely.

According to the standard model the rabbits were treated by removing the splint daily for 2–3 minutes for forcible and rapid manipulation of the knee.

IP$_3$ was administered via subcutaneously operated osmotic minipumps to three rabbits. The dose level was 1 mg/kg/hour, and the time of application period was 14–21 days. The control group, another three rabbits received NaCl-solution by osmotic minipumps.

Anteposterior and lateral radiographs were made to the hind limbs of all rabbits weekly throughout the duration of the experiment which lasted 42 days.

At the end of the experiment the rabbits were killed with an overdose of Mebunat and the left and right femoral bones of each rabbit were dissected and boiled for macroscopic examination.

The amount and localization of HB formation in the rabbits after the experimental period are shown in Table 1.

TABLE 1

Treatment and final average amount of heterotopic bone in different groups

| Group of animals | Treatment | Application of IP$_3$ | Amount of HB |
|---|---|---|---|
| Control | 1 mm | 0 | +++ |
| Control | 1 mm | 0 | ++++ |
| Control | 1 mm | 0 | +++ |
| Experim. | 1 mm | 14 days | + |
| Experim. | 1 mm | 14 days | 0 |
| Experim. | 1 mm | 21 days | 0 |

HB = heterotopic bone
1 mm = immobilization
++++ = very marked amount of HB
+++ = marked amount of HB
++ = between slight and marked amount of HB
+ slight amount of HB
0 = none amount of HB The final HB formation in the control group developed in the same way and to the same extent as has been previously found in corresponding manipulation experiments.

The animals which received IP$_3$ subcutaneously were found to have drastically less ectopic bone in the femur than the control animals.

The results obtained in the experiment indicate that the occurrence, the amount and the localization of HB formation in the rabbits could be blocked by the administration of IP$_3$.

EXAMPLE 6

Growth factor activity is considered to be involved in the process of viral infections. Viral isolates from HIV-infected patients were used in order to induce an infection by adding peripheral blood mononuclear cells (PBMC) to a medium containing different concentrations of the sodium salt of D-3,4,5-tri-O-hexanoyl-myo-inositol-1,2,6-trisphosphate (PP10-202) 25 CCID$_{50}$ (50% cell culture infections dose) of PBMC from HIV-infected patients were incubated with four different concentrations of PP10-202; 0.0625 mg/ml. 0.125 mg/ml, 0.250 mg/ml and 0.500 mg/ml. Another preparation, without any PP10-202 served as a control. The growth medium consisted of 10% fetal calf serum, 2 $\mu$M glutamine, 100 IU/ml penicillin, 100 IU/ml streptomycin and 20 $\mu$g/ml gentamicin. The concentration of cells were 2×10$^5$ per ml. All preparations were incubated for 1 hour at 37° C.

PBMCs from healthy donors were then added to the preparation. Before addition, these cells were stimulated for three days with phytohemagglutinin (PHA) 0.5×10$^6$ PHA-stimulated PBMCs were added to each preparation, followed by incubation for 3 hours at 37° C. After extensive washing the cells were resuspended in growth medium supplemented with 10 IU/ml of interleukin-2 and seeded in quadruplicates of 100,000 cells in a 96-well microtite plate before further cultivation for 7 days. The HIV-antigen production was assayed at the seventh day using an ELISA-technique. The obtained values were normalized and are summarized in the following table:

| Concentration of PP10-202 mg/ml | HIV-infection (%) |
|---|---|
| 0 | 100 |
| 0.0625 | 75 |
| 0.125 | 41 |
| 0.250 | 33 |
| 0.500 | 20 |

The results show that PP10-202 posses a strong effect to counteract the viral infection.

EXAMPLE 7

Vascular permeability factor (VPF) promotes extravasation and oedema formation Evans Blue was injected intravenously to 15 guinea pigs. This dye binds to plasma proteins and thereby provides a marker for vascular permeability to macromolecules.

One group of animals, 7 guinea pigs received an intravenous injection of 5 mg/kg D-myo-inositol-1,2,6-trisphosphate (IP$_3$) while the other group of animals, 8 guinea pigs serves as a control group.

50 mg of VPF was injected to each animal and the distribution of Evans Blue was measured.

After 60 minutes, the control group had an average area covered with Evans Blue of 62 mm$^2$ while the group which received IP$_3$ had an average area covered with Evans Blue of 15 mm$^2$.

The results show that the treatment with IP$_3$ markedly reduces the permeability caused by VPF. It has been shown that antibodies directed to VPF demonstrates a similar effect indicating that IP$_3$ has a regulating effect on VPF.

EXAMPLE 8

Growth factors are implicated to participate in inflammatory conditions. Carrageenan (0.1 ml, 1%) was injected intraplantarly in one hind paw of two groups of mice, five animals in each group.

An intravenous injection of 64 mg/kg of 1,2-O-ethylene-$\beta$-fructopyranoside- 2,3,4-trisphosphate (PP35-405) was administered immediately before the injection of carrageenan.

Injection of carrageenan induces inflammation which is measured by comparing the increase in paw volume using a plethysmometer.

After 3.5 hrs a comparison shows that the inflammation was retarded by 51% in the group recieving PP35-405. Thus the administration of PP35-405 significantly counteract the inflammatory conditions.

EXAMPLE 9

In a procedure similar to the one described in Example 8, an intravenous injection of 1,5-dideoxy-1,5-imino-N-(2-phenylethyl)arabinitol-2,3,4-trisphosphate (PP35-508) was administered.

3,5 hrs after the injection of carrageenan, the inflammation was retarded with 275 in the group recieving PP35-508. Thus the administration of PP35-508 markedly retard the inflammatory condition.

EXAMPLE 10

In a procedure similar to the one described in Example 8, an intravenous injection of myo-inositol-1,2,6-tris (carboxymethyl phosphonate) (PP40-402) was administered. 3.5 hrs after the injection of carrageenan the inflammation was retarded with 32% in the group recieving PP40-402. Thus the administration of PP40-402 markedly reduces the inflammatory condition.

EXAMPLE 11

Growth factors are involved in processes occurring in new-born mammals. The biological process of eye opening is one example where specific growth factors affect the timing and completeness of the event.

Three groups of mice, 40 animals in each group were used. One group recieved daily injections of D-myo-inositol-1,2,6-trisphosphate, sodium salt ($IP_3$) from day 0 to day 7 (192 µg/g/day) while the second group received saline under a similar regime. The third group served as a control without any treatment.

Eye opening was significantly delayed in the group recieving $IP_3$. As a medium value, eyes were opened after 13.6 and 13.5 days respectively in the groups serving as a blank control, respectively. The medium value for the group recieving $IP_3$ was 15.3 days, i.e. nearly two days delay in eye opening. These results demonstrate the growth factor, modulating activity of $IP_3$.

EXAMPLE 12

In order to investigate the effect of D-myo-inositol-1,2, 6-trisphosphate ($IP_3$) on the process of scarr formation on skin scratches to the epidermis of the back of a human hand was performed with a knife. To two of the scratches a solution comprising $IP_3$ was applied topically while two of the scratches served as controls. Ocular investigation was performed every day over a period of 10 days.

It was observed that the scratches treated with $IP_3$ formed scarr in a delayed manner compared to the control and that the formation of the scars occurred in a more smooth way. The existing scarrs after the $IP_3$-treated scratches were considered to have a nicer appearance. Thus the administration of $IP_3$ modulates the growth factor activity involved in the would healing process in a favourable way.

EXAMPLE 13

The binding of D-myo-inositol-1,2,6-trisphosphate sodium salt ($IP_3$) to bovine brain clathrin assembly protein-2 (AP-2) was studied. The binding assay was done in a total volume of 100 µl buffer containing 25 nM Na HEPES pH 7.1, 1 nM EDTA, 1 nM DTT, 5 mg/ml IgG, 10 nM tritiated inositoltetraphosphate and 1.46 µg of AP-2. The concentration of $IP_3$ ranged from 0.04 to 30 µM. Incubation was carried out on ice for a period of ten minutes and then the protein was co-precipitated with IgG using 5% (w/w) polyethylene glycol and pelleted by centrifugation at 95000 rpm for 10 minutes. The supernatants were aspirated, the pellets were wasted with 0.2 ml water and resuspended in 0.2 ml water and transferred to scintillation vials. 5.0 ml of cyto scint fluid was added to each vial and the radioactivity was measured $IP_3$ was found to compete with inositoltetraphosphate for binding. The $IC_{50}$ was determined to be 0.60±0.1 µM.

The observed binding affinity is well within the concentrations of $IP_3$ when administered to animals in different pharmacological models and supports the property of $IP_3$ to modulate the activity of certain growth factors via retarding or inhibiting the internalisation process.

EXAMPLE 14

The interaction between a polyamine, spermine and different triphosphorylated compounds were investigated in order to determin the binding constants. Spermine is a basic polyamine comprising domains of similar basicity to basic domains in growth factors. Spermine and the different phosphorylated compounds forms different complexes and the 1:1:5 complex was used as the complex for determination of binding constants.

The following binding constants, log $K_S$ was determined in 0.1 M N-tetramethylbromide at 25° C.

Compound log $K_S$

D-myo-inositol-1,2,6-trisphosphate 5.16

D-3,4,5-tri-O-hexanoyl-myo-inositol-1,2,6-trisphosphate, PP10-202 4.20

D-3,4,5-tri-O-phenylcarbamoyl-myo-inositol-1,2,6-trisphosphate, PP11-201 4.71

Methyl-6-O-butyl-α-D-mannopyranoside 2,3,4-trisphosphate, PP35-402 5.36

Trimethylolpropane trisphosphate PP50-202 <1

The results show that the cyclic moieties have binding constants, log $K_S$, higher than 4 indicating a strong binding, while the linear compound PP50-202 does not bind.

EXAMPLE 15

Two groups of mice, 10 animals per group, were used in order to investigate the analgetic effect of methyl α-D-rhamnopyranoside-2,3,4-trisphosphate (PP 35-406). The control group was given an intravenous dose of saline while the other group was given a dose of 64 mg/kg of the sodium salt of PP 35-406. Three minutes after intravenous dosing, each rat received an intraperitoneal injection of 1 ml of a 1% (w/w) solution of acetic acid. Directly after that procedure each animal was placed into individual observation chambers and the numbers of writhes elicited during the subsequent 10-minute period were recorded. After the observation period the animals were killed by cervical dislocation. The number of writhes during the observation period is an expression of the pain experienced by the animal. Percent protection was calculated as follows 10×((number of writhes in control group—number of writhes in treated animals)/(number of writhes in control group).

The protection determined for PP 35-406 was 19% demonstrating a reduction in pain when the compound is administered.

EXAMPLE 16

The enzyme phosphatidyl inositol 3' kinase (PI 3'-kinase) is implicated in a number of growth factor induced responses such as mitogenesis, chemotaxis, membrane ruffling and the balance between osteoclasts and osteoblasts. Furthermore it is known that inactivation of PI 3' kinase leads to increased oedema formation expressed as a decrease of interstitial fluid pressure ($P_{IF}$) in animal models.

An inhibitor of PI 3' kinase such as wortmannin renders a decrease of $P_{IF}$ as a consequence of inactivation of PI 3' kinase.

The measurements were performed on female Wistar Moller rats (200–250 g), anesthetized with pentobarbital (50 mg/kg i.p.).

$P_{IF}$ was measured on the dorsal side of the hind paw with sharpened glass capillarier (tip diameter 2–7 µm) filled with 0.5 M NaCl coloured with Evans Blue and connected to a serve-controlled counter pressure system. The punctures were performed through intact skin using a steromicroscope. The pipette-tip was located 0.3–0.5 mm below the skin.

Pressure measurements were made 2.5–3.0 mm from the center of injection. The normal transcapillary pressure gradient is about 0.5 mm Hg.

Three sets of experiments were performed with six animals in each set.

In the first set of experiment the vehicle for wortmannin, DMSO diluted in saline, 5 µl, was injected subdermally using a chromatography syringe. In this control group the $P_{IF}$ stayed constant at ca −0.7 mm Hg over the entire determination, on period of 100 minutes. In the second set of experiments, wortmannin 2.3 M in DMSO/saline, 5 µl was injected. The measurement of $P_{IF}$ showed a decrease to −2.5 mm Hg after 30 minutes. This value stayed constant over the subsequent determination period.

In the third set of experiments, the animals were pretreated with an intravenous injection of D-myo-inositol-1,2,6-trisphosphate ($IP_3$) 5 µg of 0.1 ml before the administration of wortmannin, 2.3 M in DMSO/saline.

The pretreatment with $IP_3$ inhibited the effect of wortmannin which resulted in an abolished decrease in $P_{IF}$.

The results demonstrate an interaction of $IP_3$ with the PI 3' kinase pathway i.e. a pathway implicated in growth factor induced responses.

EXAMPLE 17

In an experimental model of prostate tumours the effect of D-myo-inositol-1,2,6- trisphosphate ($IP_3$) was assessed. The injection of a specific cell-line Wish tumour cells, induces proliferation of osteoblasts on the calvaria of nude mice leading to bone tumours.

Ten mice were divided into two groups, one group receiving an infusion of $IP_3$ for 14 days while the other group, serving as a control group, received saline for 14 days.

$IP_3$ and saline respectively were administered with osmotic minipumps (Alzet$^R$) with a dosage of 120 mg/kg/day.

Wish cells (American Type Culture Collection$^R$, ATCC (R) F-12784 25 CCL WITH x01166) were used for inocculation. Cells were grown on MEM supplemented with 15% FCS, 2% glutamine and streptomycin-penicillin/garamycin. Cells were grown as a monolayer and trypsinised and split in the ratio 1:3 to 1:4. All together 360 million cells were harvested and suspended in 7 ml for a final concentration of approximately 10 million cells per 0.2 ml.

The osmotic pumps with $IP_3$ and saline respectively were implanted on the same day as the inoculation of Wish-cells were performed.

A 27 gauge needle on a 1 ml syringe was used for the injections of Wish-cells. The injection was done under the skin of the calvaria scratching the periosteum At day 13 all animals were given an intraperiotoneal injection of demeclocycline (Sigma Chemicals Co. St. Louis). All animals were investigated regarding the occurrence of and size of tumours. The size of tumours were measured according to a scale from + which represents small and non-severe tumours to ++++ which represents large and severe tumours.

The results are shown in the following table:

| Animal no | Treatment | Severeness of tumours |
|---|---|---|
| 1 | $IP_3$ | ++ |
| 2 | " | ++ |
| 3 | " | +++ |
| 4 | " | ++++ |
| 5 | Saline | ++++ |
| 6 | " | ++++ |
| 7 | " | ++++ |
| 8 | " | ++++ |
| 9 | " | ++++ |
| 10 | " | ++++ |

The animals receiving $IP_3$ showed a lower degree of size and severeness of the tumours which demonstrates that the administration of $IP_3$ counteracts tumour formation in a bond tumour model.

EXAMPLE 18

Injection of basic fibroblast growth factor (b FGF) stimulates osteoblastic activity and leads to bone formation. In an experiment in mice the effect of D-myo-inositol- -1,2,6-trisphosphate ($IP_3$) to counteract the growth factor induced process was assessed.

One group with five mice received an infusion of $IP_3$ for 14 days while another group of five mices, serving as a control group, received saline for 14 days.

$IP_3$ and saline respectively were administered with osmotic minipumps (Alzet$^R$) with a dosage of 120 mg/kg/day.

The osmotic minipumps were implanted on day 1.

To the calvaria of each animal, 10 µl of b FGF (concentration 50 µg/m) was injected four times daily of the period of day 2 to 4.

After the experimental period of 14 days each animal was investigated macroscopically and the histological preparations were further examined by conventional routines.

Macroscopically visible bone formation was measured according to scale from 0 which represents no bone formation to ++++ which represents severe bone formation The results are shown in the following table:

| Animal no | Treatment | Severeness of bone formation |
|---|---|---|
| 1 | $IP_3$ | 0 |
| 2 | " | ++ |
| 3 | " | 0 |
| 4 | " | 0 |
| 5 | " | 0 |
| 6 | Saline | ++++ |
| 7 | " | ++++ |
| 8 | " | ++++ |
| 9 | " | ++++ |
| 10 | " | ++++ |

The results show that $IP_3$ has a strong counteractive effect against b FGF-induced bone formation. Furthermore the histological examination showed clear differences between the group expressed as structure and thickness of the calvaria. The preparation show that $IP_3$ has anti-angiogenic properties.

EXAMPLE 19

The interaction between D-myo-inositol-1,2,6-trisphosphate ($IP_3$) and several growth factors has been examined by the utilization of computer modelling programs.

Especially the interaction between $IP_3$ and the fibroblast growth factor family reveals the pattern that the two axial and one equatorial phosphate group interacts with regions consisting of basic amino acids such as lysine, arginine and histidine. These domain are essential for the dimerization of growth factors but also for the interaction between growth factors and their cellular receptors.

In the interaction between $IP_3$ and acid Fibroblast Growth Factor (a FGF) specific binding is observed with lysine 112, lysine 118 and arginine 122 in such a manner that the distance is approximately 2 Å indicating strong and firm interactions.

Furthermore $IP_3$ interacts in a very specific way with basic Fibroblast Growth Factor (b FGF). the different phosphates groups of $IP_3$ interacts with arginine 120, distance 1.94 Å, with lysine 125, distance 2.40 Å, with lysine 135, distance 2.37 Å and with aspargine 27; distance 2.68 Å. A specific interaction is observed to the site in b FGF where the dimerization process is initiated. To this site $IP_3$ interacts with arginine 72, distance 2.26 Å, with arginine 81; distance 2.36 Å and arginine 39; distance 1.45 Å.

On of the essential elements of the interaction is the fact that the three phosphate groups of $IP_3$ stereochemically is in a form where two moities are axial and one equatorial. As a consequence $IP_3$ can be regarded as a model substance where the same type of interactions can be foreseen with other stereochemically similar compounds according to the invention.

What is claimed is:

1. A method of treating inflammatory conditions comprising administering to a mammal in need thereof an effective amount of a monosaccharide, in which said monosaccharide is substituted by at least three vicinal phosphorus containing radicals of the formula:

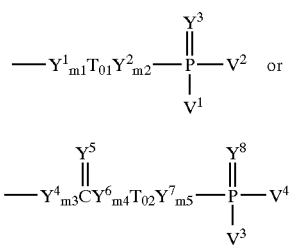

wherein $V^1$ to $V^4$ are independently $Y^8_{m6}T_{o3}U$;

$T_{01}$ to $T_{03}$ are independently $(CH_2)_n$, CH=CH, or $CH_2CH=CHCH_2$;

o1 to o3 are independently 0 or 1;

n is 0 to 4;

U is $R^1Y^9m_7$, $CY^{10}Y^{11}R^2$, $SY^{12}Y^{13}Y^{14}R^3$, $PY^{15}Y^{16}Y^{17}R^4R^5$, $Y^{18}PY^{19}Y^{20}Y^{21}R^6R^7$, $CH_2NO_2$, $NHSO_2R^8$, or $NHCY^{22}Y^{23}R^9$;

m1 to m7 are independently 0 to 1;

$Y^1$ to $Y^{23}$ are independently $NR^{10}$, $NOR^{11}$, O, or S;

and where $R^1$ to $R^{11}$ are independently i) hydrogen;

ii) a straight or branched saturated or unsaturated alkyl group containing 1–22 carbon atoms;

iii) a saturated, unsaturated aromatic or non-aromatic homo- or heterocyclic group containing 3–22 carbon atoms and 0–5 heteroatoms selected from the group consisting of nitrogen, oxygen and sulfur;

iv) a straight or branched saturated or unsaturated alkyl group containing 1–22 carbon atoms substituted with a saturated or unsaturated aromatic or non-aromatic homo- or heterocyclic group containing 3–22 carbon and 0–5 heteroatoms selected from the group consisting of nitrogen, oxygen, and sulfur;

v) an aromatic or non-aromatic homo-or heterocyclic group containing 3–22 carbon and 0–5 heteroatoms selected from the group consisting of nitrogen, oxygen, and sulfur which aromatic or non-aromatic homo-or heterocyclic group is substituted with a straight or branched saturated or unsaturated group containing 1–22 carbon atoms;

whereby said groups in ii–v are unsubstituted or are substituted by 1–6 of the following groups: hydroxy, alkoxy, aryloxy, acyloxy, carboxy, alkoxycarbonyl, alkoxycarbonyloxy, aryloxycarbonyl, aryloxycarbonyloxy, carbamoyl, fluoro, chloro, bromo, azido, cyano, oxo, oxa, amino, imino, alkylamino, arylamino, acylamino, arylazo, nitro, alkylthio or alkysulfonyl.

2. The method according to claim 1 wherein the inflammatory conditions is rheumatoid arthritis.

3. The method according to claim 1 or 2 wherein the phosphorus-containing radicals have the following formula:

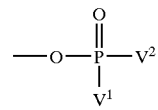

wherein $V^1$ and $V^2$ are OH, $(CH_2)_pOH$, COOH, $CONH_2$, CONOH, $(CH_2)_pCOOH$, $(CH_2)_pCONH_2$, $(CH_2)_pCONOH$, $(CH_2)_pSO_3H$, $(CH_2)_pSO_3NH_2$, $(CH_2)_pNO_2$, $(CH_2)_pPO_3H_2$, $O(CH_2)_pOH$, $O(CH_2)_pCOOH$, $O(CH_2)_pCONH_2$, $O(CH_2)_pCONOH$, $O(CH_2)_pSO_3H$, $O(CH_2)_pSO_3NH_2$, $O(CH_2)_pNO_2$, $O(CH_2)_pPO_3H_2$ or $CF_2COOH$; and p is 1 or 4.

4. The method according to claim 1 or 2 wherein the phosphorus-containing radicals are phosphate groups.

5. The method according to claim 1 or 2 wherein the cyclic compound is a monosaccharide.

6. The method according to claim 5 wherein the monosaccharide is D/L-ribose, D/L-arabinose, D/L-xylose, D/L-lyxose, D/L-allose, D/L-altrose, D/L-glucose, D/L-mannose, D/L-gulose, D/L-idose, D/L-galactose, D/L-talose, D/L-ribulose, D/L-xylulose, D/L-psicose, D/L-sorbose, D/L-tagatose, or D/L-fructose.

7. The method according to claim 5 wherein the monosaccharide is substituted with three phosphorus-containing radicals having the following formula:

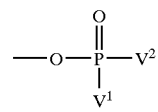

wherein $V^1$ and $V^2$ are OH, $(CH_2)_pOH$, COOH, $CONH_2$, CONOH $(CH_2)_pCOOH$, $(CH_2)_pCONH_2$, $(CH_2)_pCONOH$, $(CH_2)_p SO_3H$, $(CH_2)_pSO_3NH_2$, $(CH_2)_pNO_2$, $(CH_2)_p PO_3H_2$, $O(CH_2)_pOH$, $O(CH_2)_pCOOH$, $O(CH_2)_p CONH_2$, $O(CH_2)_pCONOH$, $O(CH_2)_pSO_3H$, $O(CH_2)_p SO_3NH_2$, $O(CH_2)_pNO_2$, $O(CH_2)_pPO_3H_2$ or $CF_2COOH$; and p is 1 to 4.

8. The method according to claim 7 wherein the phosphorous containing radicals are phosphate groups.

9. The method according to claim 1 or 2 wherein the cyclic compound administered to the mammal is selected from the group consisting of mannose-2,3,4- trisphosphate, rhamnose-2,3,4-trisphosphate, galactose-2,3,4-trisphosphate, methyl-6-O- butyl-α-D-mannopyranoside-2,3,4-trisphosphate, 1,5-anhydro-D-arabinitol-2,3,4-trisphosphate, fructose-2,3,4-trisphosphate, 1,2-O-ethylene-β-D-fructopyranoside-2,3,4- trisphosphate, cyclohexane-1,2,3-triol trisphosphate, 1,5-dideoxy-1,5-iminoarabinitol-2,3,4- trisphosphate, altrose-2,3,4-trisphosphate, or methyl-6-O-butyl-αD-altropyranoside 2,3,4-trisphosphate.

10. The method according to claim 1 or 2 wherein the compound is administered by parenteral or non-parenteral administration.

11. The method according to claim 1 or 2 wherein the effective amount ranges from about 0.1 to about 100 mg per kg body weight of the mammal.

* * * * *